(12) United States Patent
Schultz

(10) Patent No.: US 7,549,995 B2
(45) Date of Patent: Jun. 23, 2009

(54) SURGICAL INSTRUMENT FOR HANDLING AN IMPLANT

(75) Inventor: Robert Schultz, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 110 days.

(21) Appl. No.: 10/886,245

(22) Filed: Jul. 7, 2004

(65) Prior Publication Data

US 2005/0033305 A1 Feb. 10, 2005

(30) Foreign Application Priority Data

Jul. 8, 2003 (DE) .............................. 103 30 699

(51) Int. Cl.
*A61B 17/58* (2006.01)

(52) U.S. Cl. .................................................. 606/99

(58) Field of Classification Search ... 623/17.11–17.16; 606/53, 86, 99, 211, 86 A
See application file for complete search history.

(56) References Cited

U.S. PATENT DOCUMENTS

| | | |
|---|---|---|
| 3,426,364 A | 2/1969 | Lumb |
| 3,867,728 A | 2/1975 | Stubstad et al. |
| 3,875,595 A | 4/1975 | Froning |
| 4,309,777 A | 1/1982 | Patil |
| 4,759,766 A | 7/1988 | Buettner-Janz et al. |
| 4,759,769 A | 7/1988 | Hedman et al. |
| 4,863,476 A | 9/1989 | Shepperd |
| 4,863,477 A | 9/1989 | Monson |
| 4,911,718 A | 3/1990 | Lee et al. |
| 5,002,576 A | 3/1991 | Fuhrmann et al. |
| 5,122,130 A | 6/1992 | Keller |
| 5,123,926 A | 6/1992 | Pisharodi |
| 5,236,460 A | 8/1993 | Barber |
| 5,258,031 A | 11/1993 | Salib et al. |
| 5,306,308 A | 4/1994 | Gross et al. |
| 5,314,477 A | 5/1994 | Marnay |

(Continued)

FOREIGN PATENT DOCUMENTS

DE 30 23 353 A1 4/1981

(Continued)

OTHER PUBLICATIONS

Szpalski, Marek, Gunzburg, Robert, and Mayer, Michael, "Spine Arthroplasty: A Historical Review", Eur Spine J (2002), 11 (Suppl. 2), pp. S65-S84.

(Continued)

*Primary Examiner*—Eduardo C Robert
*Assistant Examiner*—Michael J Araj
(74) *Attorney, Agent, or Firm*—RatnerPrestia

(57) ABSTRACT

An implant has two parts, each of which includes a joint surface facing the other part, wherein the joint surfaces are in contact with one another in an implanted state and permit pivoting of the two parts in relation to one another. An instrument for handling the implant includes a holding element for detachably connecting the instrument with each of the two parts of the implant. The instrument further includes a spacer element extending between the parts of the implant when the parts are connected with the instrument and maintaining a distance between the parts, thereby preventing the joint surfaces of the two parts of the implant from contacting each other.

20 Claims, 3 Drawing Sheets

U.S. PATENT DOCUMENTS

| | | | |
|---|---|---|---|
| 5,370,697 A | 12/1994 | Baumgartner | |
| 5,397,364 A * | 3/1995 | Kozak et al. | 623/17.11 |
| 5,401,269 A | 3/1995 | Büttner-Janz et al. | |
| 5,425,773 A | 6/1995 | Boyd et al. | |
| 5,507,816 A | 4/1996 | Bullivant | |
| 5,534,030 A | 7/1996 | Navarro et al. | |
| 5,556,431 A | 9/1996 | Büttner-Janz | |
| 5,562,738 A | 10/1996 | Boyd et al. | |
| 5,674,294 A | 10/1997 | Bainville et al. | |
| 5,674,296 A | 10/1997 | Bryan et al. | |
| 5,676,635 A | 10/1997 | Levin | |
| 5,676,701 A | 10/1997 | Yuan et al. | |
| 5,683,465 A | 11/1997 | Shinn et al. | |
| 5,702,449 A | 12/1997 | McKay | |
| 5,782,830 A | 7/1998 | Farris | |
| 5,782,832 A | 7/1998 | Larsen et al. | |
| 5,824,094 A | 10/1998 | Serhan et al. | |
| 5,827,328 A | 10/1998 | Buttermann | |
| 5,865,846 A | 2/1999 | Bryan et al. | |
| 5,888,226 A | 3/1999 | Rogozinski | |
| 5,888,227 A | 3/1999 | Cottle | |
| 5,893,889 A | 4/1999 | Harrington | |
| 5,968,051 A * | 10/1999 | Luckman et al. | 606/88 |
| 5,989,291 A | 11/1999 | Ralph et al. | |
| 6,001,130 A | 12/1999 | Bryan et al. | |
| 6,019,793 A | 2/2000 | Perren et al. | |
| 6,039,763 A | 3/2000 | Shelokov | |
| 6,063,121 A | 5/2000 | Xavier et al. | |
| 6,083,225 A | 7/2000 | Winslow et al. | |
| 6,102,950 A * | 8/2000 | Vaccaro | 623/17.16 |
| 6,113,637 A * | 9/2000 | Gill et al. | 623/17.15 |
| 6,113,639 A | 9/2000 | Ray et al. | |
| 6,127,597 A | 10/2000 | Beyar et al. | |
| 6,139,579 A | 10/2000 | Steffee et al. | |
| 6,156,067 A | 12/2000 | Bryan et al. | |
| 6,162,252 A | 12/2000 | Kuras et al. | |
| 6,176,881 B1 | 1/2001 | Schär et al. | |
| 6,200,322 B1 | 3/2001 | Branch et al. | |
| 6,210,442 B1 | 4/2001 | Wing et al. | |
| 6,224,599 B1 * | 5/2001 | Baynham et al. | 606/61 |
| 6,231,609 B1 | 5/2001 | Mehdizadeh | |
| 6,296,664 B1 | 10/2001 | Middleton | |
| 6,348,071 B1 | 2/2002 | Steffee et al. | |
| 6,368,350 B1 | 4/2002 | Erickson et al. | |
| 6,395,032 B1 | 5/2002 | Gauchet | |
| 6,419,706 B1 | 7/2002 | Graf | |
| 6,443,987 B1 | 9/2002 | Bryan | |
| 6,443,990 B1 | 9/2002 | Aebi et al. | |
| 6,468,310 B1 | 10/2002 | Ralph et al. | |
| 6,517,580 B1 | 2/2003 | Ramadan et al. | |
| 6,524,341 B2 | 2/2003 | Läng et al. | |
| 6,527,804 B1 | 3/2003 | Gauchet et al. | |
| 6,527,806 B2 | 3/2003 | Ralph et al. | |
| 6,533,818 B1 | 3/2003 | Weber et al. | |
| 6,540,785 B1 | 4/2003 | Gill et al. | |
| 6,558,424 B2 * | 5/2003 | Thalgott | 623/17.16 |
| 6,562,072 B1 | 5/2003 | Fuss et al. | |
| 6,572,653 B1 | 6/2003 | Simonson | |
| 6,575,899 B1 | 6/2003 | Foley et al. | |
| 6,579,320 B1 | 6/2003 | Gauchet et al. | |
| 6,579,321 B1 | 6/2003 | Gordon et al. | |
| 6,582,466 B1 | 6/2003 | Gauchet | |
| 6,582,468 B1 | 6/2003 | Gauchet | |
| 6,607,558 B2 | 8/2003 | Kuras | |
| 6,610,092 B2 | 8/2003 | Ralph et al. | |
| 6,613,090 B2 | 9/2003 | Fuss et al. | |
| 6,626,943 B2 | 9/2003 | Eberlein et al. | |
| 6,645,248 B2 | 11/2003 | Casutt | |
| 6,645,249 B2 | 11/2003 | Ralph et al. | |
| 6,656,224 B2 | 12/2003 | Middleton | |
| 6,666,889 B1 | 12/2003 | Commarmond | |
| 6,669,730 B2 | 12/2003 | Ralph et al. | |
| 6,669,732 B2 | 12/2003 | Serhan et al. | |
| 6,673,113 B2 | 1/2004 | Ralph et al. | |
| 6,682,562 B2 | 1/2004 | Viart et al. | |
| 6,706,068 B2 | 3/2004 | Ferree | |
| 6,719,796 B2 | 4/2004 | Cohen et al. | |
| 6,723,097 B2 | 4/2004 | Fraser et al. | |
| 6,723,127 B2 | 4/2004 | Ralph et al. | |
| 6,726,720 B2 | 4/2004 | Ross et al. | |
| 6,733,532 B1 | 5/2004 | Gauchet et al. | |
| 6,736,850 B2 | 5/2004 | Davis | |
| 6,740,117 B2 | 5/2004 | Ralph et al. | |
| 6,740,118 B2 | 5/2004 | Eisermann et al. | |
| 6,740,119 B2 | 5/2004 | Ralph et al. | |
| 6,758,861 B2 | 7/2004 | Ralph et al. | |
| 6,764,515 B2 | 7/2004 | Ralph et al. | |
| 6,770,094 B2 | 8/2004 | Fehling et al. | |
| 6,770,095 B2 | 8/2004 | Grinberg et al. | |
| 6,793,678 B2 | 9/2004 | Hawkins | |
| 6,802,867 B2 | 10/2004 | Manasas et al. | |
| 6,827,740 B1 | 12/2004 | Michelson | |
| 2001/0016773 A1 | 8/2001 | Serhan et al. | |
| 2002/0035400 A1 | 3/2002 | Bryan et al. | |
| 2002/0107573 A1 | 8/2002 | Steinberg | |
| 2002/0111681 A1 | 8/2002 | Ralph et al. | |
| 2003/0009223 A1 | 1/2003 | Fehling et al. | |
| 2003/0014112 A1 | 1/2003 | Ralph et al. | |
| 2003/0028197 A1 * | 2/2003 | Hanson et al. | 606/99 |
| 2003/0040802 A1 | 2/2003 | Errico et al. | |
| 2003/0065395 A1 | 4/2003 | Ralph et al. | |
| 2003/0069586 A1 | 4/2003 | Errico et al. | |
| 2003/0069643 A1 | 4/2003 | Ralph et al. | |
| 2003/0074066 A1 | 4/2003 | Errico et al. | |
| 2003/0074067 A1 | 4/2003 | Errico et al. | |
| 2003/0074068 A1 | 4/2003 | Errico et al. | |
| 2003/0074069 A1 | 4/2003 | Errico et al. | |
| 2003/0074070 A1 | 4/2003 | Errico et al. | |
| 2003/0074071 A1 | 4/2003 | Errico et al. | |
| 2003/0074072 A1 | 4/2003 | Errico et al. | |
| 2003/0074073 A1 | 4/2003 | Errico et al. | |
| 2003/0074074 A1 | 4/2003 | Errico et al. | |
| 2003/0078590 A1 | 4/2003 | Errico et al. | |
| 2003/0078663 A1 | 4/2003 | Ralph et al. | |
| 2003/0078666 A1 | 4/2003 | Ralph et al. | |
| 2003/0135277 A1 | 7/2003 | Bryan et al. | |
| 2003/0176923 A1 | 9/2003 | Keller et al. | |
| 2003/0187454 A1 | 10/2003 | Gill et al. | |
| 2003/0187506 A1 | 10/2003 | Ross et al. | |
| 2003/0220691 A1 | 11/2003 | Songer et al. | |
| 2003/0229355 A1 * | 12/2003 | Keller | 606/99 |
| 2003/0229358 A1 | 12/2003 | Errico et al. | |
| 2003/0233146 A1 | 12/2003 | Grinberg et al. | |
| 2003/0236520 A1 | 12/2003 | Lim et al. | |
| 2003/0236571 A1 | 12/2003 | Ralph et al. | |
| 2004/0002761 A1 | 1/2004 | Rogers et al. | |
| 2004/0002762 A1 | 1/2004 | Hawkins | |
| 2004/0010316 A1 | 1/2004 | William et al. | |
| 2004/0024462 A1 | 2/2004 | Ferree et al. | |
| 2004/0034420 A1 | 2/2004 | Errico et al. | |
| 2004/0034421 A1 | 2/2004 | Errico et al. | |
| 2004/0034422 A1 | 2/2004 | Errico et al. | |
| 2004/0034424 A1 | 2/2004 | Errico et al. | |
| 2004/0034425 A1 | 2/2004 | Errico et al. | |
| 2004/0034426 A1 | 2/2004 | Errico et al. | |
| 2004/0059318 A1 | 3/2004 | Zhang et al. | |
| 2004/0073310 A1 | 4/2004 | Moumene et al. | |
| 2004/0073312 A1 | 4/2004 | Eisermann et al. | |
| 2004/0078079 A1 | 4/2004 | Foley | |
| 2004/0083000 A1 | 4/2004 | Keller et al. | |
| 2004/0093088 A1 | 5/2004 | Ralph et al. | |
| 2004/0098130 A1 | 5/2004 | Ralph et al. | |
| 2004/0098131 A1 | 5/2004 | Bryan et al. | |
| 2004/0102849 A1 | 5/2004 | Ralph et al. | |

| | | | |
|---|---|---|---|
| 2004/0111156 A1 | 6/2004 | Ralph et al. | |
| 2004/0117021 A1 | 6/2004 | Biedermann et al. | |
| 2004/0117022 A1* | 6/2004 | Marnay et al. | 623/17.16 |
| 2004/0133281 A1 | 7/2004 | Khandkar et al. | |
| 2004/0143331 A1 | 7/2004 | Errico et al. | |
| 2004/0143332 A1* | 7/2004 | Krueger et al. | 623/17.14 |
| 2004/0148027 A1 | 7/2004 | Errico et al. | |
| 2004/0158325 A1 | 8/2004 | Errico et al. | |
| 2004/0158328 A1 | 8/2004 | Eisermann | |
| 2004/0167534 A1 | 8/2004 | Errico et al. | |
| 2004/0167536 A1 | 8/2004 | Errico et al. | |
| 2004/0167537 A1 | 8/2004 | Errico et al. | |
| 2004/0167626 A1 | 8/2004 | Geremakis et al. | |
| 2004/0193158 A1 | 9/2004 | Lim et al. | |
| 2004/0220582 A1* | 11/2004 | Keller | 606/99 |
| 2004/0220668 A1 | 11/2004 | Eisermann et al. | |
| 2004/0220670 A1 | 11/2004 | Eisermann et al. | |
| 2004/0220677 A1 | 11/2004 | Delfosse et al. | |
| 2004/0225362 A1 | 11/2004 | Richelsoph | |
| 2004/0225363 A1 | 11/2004 | Richelsoph | |
| 2004/0225364 A1 | 11/2004 | Richelsoph et al. | |
| 2004/0225365 A1 | 11/2004 | Eisermann et al. | |
| 2004/0225366 A1 | 11/2004 | Eisermann et al. | |
| 2004/0243238 A1 | 12/2004 | Arnin et al. | |
| 2004/0243240 A1 | 12/2004 | Beaurain et al. | |
| 2004/0249462 A1 | 12/2004 | Huang | |
| 2005/0021042 A1* | 1/2005 | Marnay et al. | 606/99 |
| 2005/0033306 A1* | 2/2005 | Keller | 606/99 |
| 2005/0043803 A1 | 2/2005 | Schultz et al. | |
| 2005/0131542 A1* | 6/2005 | Benzel et al. | 623/17.13 |
| 2005/0143824 A1* | 6/2005 | Richelsoph et al. | 623/17.16 |
| 2005/0159819 A1* | 7/2005 | McCormack et al. | 623/17.16 |
| 2005/0228500 A1* | 10/2005 | Kim et al. | 623/17.13 |

FOREIGN PATENT DOCUMENTS

| | | | |
|---|---|---|---|
| DE | 697 22 244 T2 | 5/1998 | |
| DE | 197 10 392 C1 | 7/1999 | |
| DE | 198 16 832 C1 | 1/2000 | |
| DE | 101 52 567 A1 | 5/2003 | |
| DE | 203 10 432 U1 | 10/2003 | |
| DE | 203 10 433 U1 | 10/2003 | |
| DE | 203 11 400 U1 | 11/2003 | |
| DE | 203 13 183 U1 | 11/2003 | |
| DE | 203 15 611 U1 | 1/2004 | |
| DE | 203 15 613 U1 | 1/2004 | |
| DE | 20 2004 009 542 U1 | 9/2004 | |
| DE | 20 2004 014 119 U1 | 12/2004 | |
| EP | 0 471 821 B1 | 2/1992 | |
| EP | 0 282 161 B1 | 8/1992 | |
| EP | 0 560 140 B1 | 9/1993 | |
| EP | 0 560 141 B1 | 9/1993 | |
| EP | 0 634 157 B1 | 1/1995 | |
| EP | 1 002 500 A1 | 5/2000 | |
| EP | 1 344 507 A1 | 3/2002 | |
| EP | 1 344 508 A1 | 3/2002 | |
| EP | 1 250 898 A1 | 10/2002 | |
| EP | 0 948 299 B1 | 5/2003 | |
| EP | 1 374 808 A1 | 1/2004 | |
| EP | 1 124 509 B1 | 3/2004 | |
| EP | 1 421 922 A1 | 5/2004 | |
| EP | 1 475 059 A2 | 11/2004 | |
| FR | 2 694 882 | 2/1994 | |
| FR | 2 730 159 | 8/1996 | |
| FR | 2 799 116 | 4/2001 | |
| FR | 2 824 261 | 11/2002 | |
| JP | 06178787 A | 6/1994 | |
| WO | WO 95/26697 A1 | 10/1995 | |
| WO | WO 99/11203 | 3/1999 | |
| WO | WO 00/23015 | 4/2000 | |
| WO | WO 00/53127 | 9/2000 | |
| WO | WO 00/64385 A1 | 11/2000 | |
| WO | WO 01/01893 A1 | 1/2001 | |
| WO | WO 01/01895 A1 | 1/2001 | |
| WO | WO 01/18931 A1 | 3/2001 | |
| WO | WO 01/19295 A1 | 3/2001 | |
| WO | WO 01/64140 | 9/2001 | |
| WO | WO 01/93785 A2 | 12/2001 | |
| WO | WO 01/93786 A2 | 12/2001 | |
| WO | WO 02/054994 * | 7/2002 | 606/99 |
| WO | WO 02/080818 A1 | 10/2002 | |
| WO | WO 02/089701 A2 | 11/2002 | |
| WO | WO 03/003952 A1 | 1/2003 | |
| WO | WO 03/007779 | 1/2003 | |
| WO | WO 03/007780 A2 | 1/2003 | |
| WO | WO 03/007780 A3 | 1/2003 | |
| WO | WO 03/028595 A1 | 4/2003 | |
| WO | WO 03/039400 A2 | 5/2003 | |
| WO | WO 03/047472 A1 | 6/2003 | |
| WO | WO 03/075803 A1 | 9/2003 | |
| WO | WO 03/075804 | 9/2003 | |
| WO | WO 03/084449 A1 | 10/2003 | |
| WO | WO 03/094806 | 11/2003 | |
| WO | WO 03/099172 A1 | 12/2003 | |
| WO | WO 2004/016205 A2 | 2/2004 | |
| WO | WO 2004/019828 A1 | 3/2004 | |
| WO | WO 2004/026186 A1 | 4/2004 | |
| WO | WO 2004/039285 A2 | 5/2004 | |
| WO | WO 2004/041129 A1 | 5/2004 | |
| WO | WO 2004/041131 A2 | 5/2004 | |
| WO | WO 2004/054475 A1 | 7/2004 | |
| WO | WO 2004/054476 A1 | 7/2004 | |
| WO | WO 2004/054478 A1 | 7/2004 | |
| WO | WO 2004/054480 A1 | 7/2004 | |
| WO | WO 2004/073561 A1 | 9/2004 | |
| WO | WO 2004/084774 A1 | 10/2004 | |

OTHER PUBLICATIONS

Article from The Burton Report, "Artificial Discs", pp. 5, located at http://www.burtonreport.com/infspine/surgartificialdiscs.htm.

Traynelis, M.D., Vincent, and Haid, Jr., M.D., Regis W., "Spinal Disc Replacement: The Development of Artificial Discs", pp. 12.

Bao, Ph.D., Qi-Bin, and Yuan, M.D., Hasen A., "Artificial Disc Technology", Neurosurg Focus 9(4), 2000, 2000 American Association of Neurological Surgeons, pp. 12.

* cited by examiner

SURGICAL INSTRUMENT FOR HANDLING AN IMPLANT

This application is related to and claims the benefit of German Utility Model No. 203 10 433.1 entitled Surgical Instrument for Handling an Implant issued on Sep. 4, 2003, and German Patent Application No. 103 30 699.4-35 filed Jul. 8, 2003.

FIELD OF THE INVENTION

The present invention pertains to an inserting instrument for an intervertebral disk prosthesis. An intervertebral disk prosthesis can be inserted with this inserting instrument such that the bearing components are protected from impact pulses that may occur during the implantation.

BACKGROUND OF THE INVENTION

A surgical instrument for handling an implant is known, for example, from WO 01/19295 A1, and is used to pick up an intervertebral implant and then introduce it into the intervertebral space between two vertebral bodies. With the prior-art instrument, the two parts of the implant are introduced into the intervertebral space in such a way that they are closely in contact with one another and are then removed from one another to the extent that an inlay, which carries the joint surface, can be pushed in between them. The implant is consequently a three-part implant.

In case of the use of two-part implants, in which the two parts have a joint surface each, which are flatly in contact with one another in the inserted state and make possible the pivotability of the two parts as a result, the two parts are introduced together into the intervertebral space. Such a connection carries a risk that the joint surfaces may be damaged. This risk is especially high if the joint surfaces are sensitive, for example, if they consist of ceramic and therefore tolerate shocks very poorly. However, it is unavoidable during the implantation of the implant that such shocks are exerted on the implant, for example, when the implant is being driven into the intervertebral space.

Accordingly, there remains a need for an improved surgical instrument that reduces the risk for damage to the joint surfaces of the implant during the handling of the implant.

SUMMARY OF THE INVENTION

The present invention pertains to an implant and a surgical instrument for handling the implant. The implant includes two parts that have a joint surface each facing the other part, and which are in contact with one another in the implanted state and make possible the pivoting of the two parts in relation to one another as a result. The invention includes a holding device as a part of the instrument, by which the instrument can be detachably connected with each of the two parts.

More specifically, a spacer element is provided on the instrument, which spacer element extends between the parts of the implant when the parts of the implant are connected with the instrument and keeps these parts at such a distance from one another that the joint surfaces of the two parts do not touch each other. The two parts are consequently removed from one another to the extent that no contact can occur between the joint surfaces during the handling and especially during the insertion into the intervertebral space, so that the risk for damage to these joint surfaces due to shocks or the like is also minimized.

It is advantageous in this connection for the distance between the joint surfaces when the spacer element extends between the parts of the implant to be between 0.2 mm and 2 mm, i.e., very small, so that the overall height of the implant is increased only insignificantly for the introduction compared with the overall height that the implant has in the ready-to-function state, i.e., when the joint surfaces are in contact with one another.

The spacer element may be of a substantially plate-shaped design. It is favorable if the top side facing the parts and the underside of the spacer element are flat, and the implant preferably also has corresponding, flat surfaces in this case, so that a flat contact occurs, which minimizes the development of pressure peaks.

Provisions are made in an especially preferred embodiment for the top side facing the parts and the underside of the spacer element to be slightly sloped in relation to one another, i.e., the spacer element is slightly wedge-shaped, and the extraction of the spacer element after the implantation of the implant is facilitated hereby.

The spacer element may have a one-piece design, but provisions are made in a preferred embodiment for the spacer element to comprise two spacer members receiving the joint surfaces between them. These spacer members are located on opposite sides of the joint surfaces, e.g., of an inlay forming the joint surfaces, which inlay is inserted into the parts of the implant, so that the parts of the implant are kept symmetrically at a distance on both sides. For example, the spacer members may extend in parallel to one another, in which case they show a similarity to the prongs of a two-pronged fork.

Provisions are made in an especially preferred embodiment for the holding means and the parts of the implant to have clamping elements that can be pushed into each other for the detachable connection, which clamping elements can be braced in relation to one another at right angles to the direction in which they are pushed in. These clamping elements are not yet braced during the pushing in, and the pushing in and the extraction are possible in a simple manner as a result. However, the clamping elements are clamped due to the bracing such that it is very difficult or even impossible to pull off the parts of the implant from the holding means.

The clamping elements may be, in particular, projections and setbacks that engage one another. In a preferred embodiment, the projections and setbacks are pins and holes receiving the pins.

It is advantageous in this connection for the clamping elements to be able to be braced in relation to one another in a direction that extends at right angles to the displacement of the parts of the implant by the spacer element extending between them. Thus, the parts of the implant are not tensioned against the spacer element due to the tension of the clamping elements, but the pressing forces of the parts of the implant against the spacer element are independent from whether or not the clamping elements are tensioned.

In a preferred embodiment of the present invention, the clamping elements may be arranged at the instrument and displaceable at right angles to the direction in which the clamping elements are pushed in.

For example, provisions may be made in a preferred embodiment for the instrument to have two arms, which can be pivoted in relation to one another and which carry clamping elements for the two parts at their free ends each, and for a tensioning device, with which the arms are pivotable in relation to one another, to be arranged at the instrument. The arms may be pivoted elastically in relation to one another.

In a preferred embodiment, the tensioning device is formed by a sleeve, which extends over the arms and is movable along the arms. This sleeve is preferably rotatable around its longitudinal axis for movement along the arms and is mounted at the instrument by means of a screw thread. By rotating the sleeve, the sleeve is displaced along the arm and tensions the two arms against one another in the process. Each of the two arms may carry a spacer member.

Provisions are made in an especially preferred embodiment for each arm to carry at its free end a clamping jaw, at which clamping elements for both parts of the implant as well as a spacer member are arranged and which form a stop, with which the parts of the implant are in contact when the instrument and the implant are connected.

DETAILED DESCRIPTION OF THE INVENTION

Figure 1:
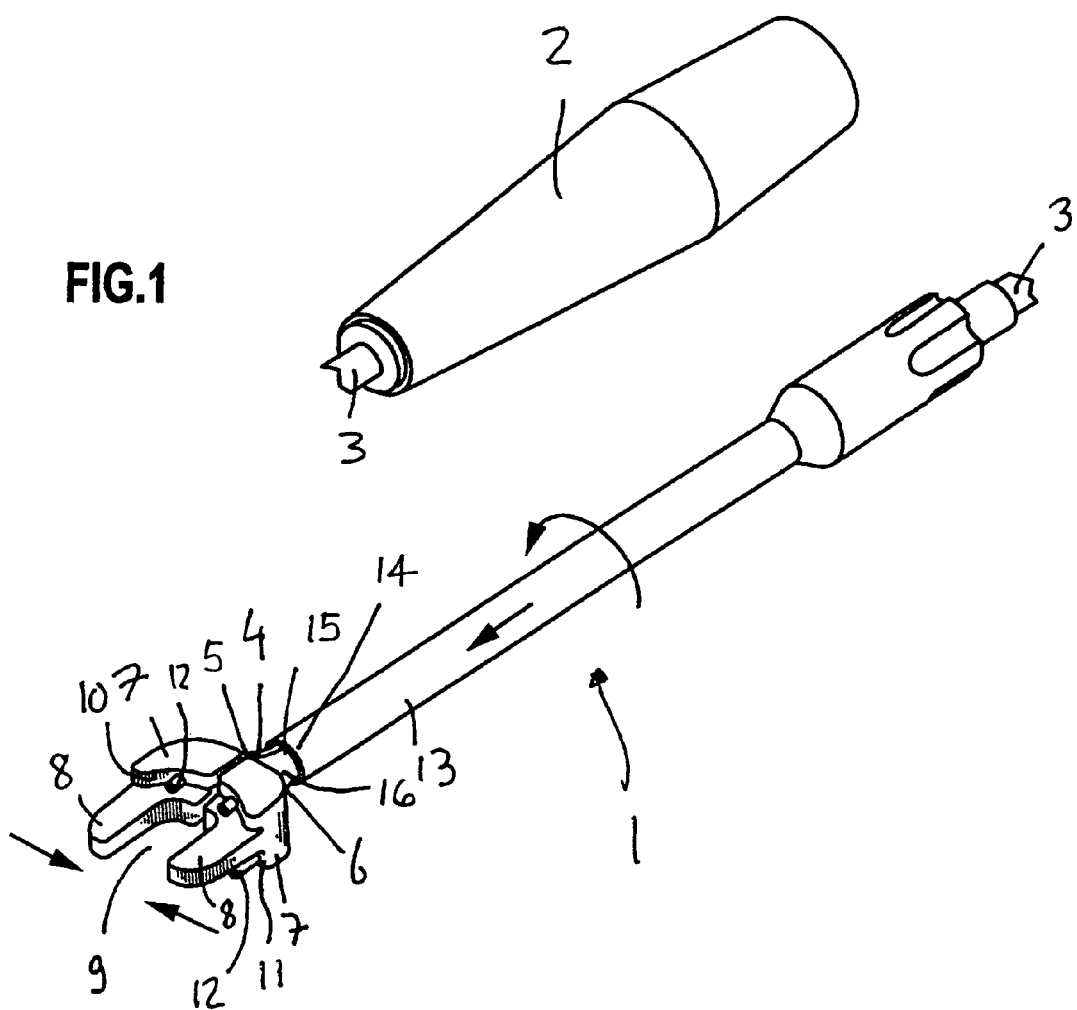
FIG. 1 shows a perspective view of a surgical instrument for handling an implant.

Although the invention is illustrated and described herein with reference to specific embodiments, the invention is not intended to be limited to the details shown. Rather, various modifications may be made in the details within the scope and range of equivalents of the claims and without departing from the invention.

The surgical instrument 1 shown in the drawings comprises a handle 2 with a bar 3 held thereon, which is divided at its end located opposite the handle 2 by a longitudinal slot 4 into two parallel arms 5, 6, which can be elastically pivoted against each other or apart from one another. The two arms 5, 6 have the same design, and only one part will therefore be described in detail below. At its end, the arm carries a clamping jaw 7, which may be made in one piece with the arm and is broader and higher than the arm. A substantially plate-shaped spacer member 8 is arranged at each clamping jaw 7, the spacer member 8 extending in the longitudinal direction of the bar 3 on the side facing away from the handle 2. The two spacer members 8 of the two clamping jaws 7 extend in the direction of the bar 3 in parallel and at spaced locations from one another, so that an intermediate space 9 is left free between the plate-shaped spacer members 8. The spacer members 8 may be designed as plates with parallel, flat top side and underside, but it is also contemplated that they have a somewhat smaller thickness toward the free end, i.e., they are slightly wedge-shaped.

The thickness of the spacer member 8 is smaller than the thickness of the clamping jaw 7, and the clamping jaws 7 form a step 10, 11 each on the top side and on the underside of the spacer member 8, and pins 12 extending in parallel to the bar 3 project from the clamping jaws 7 in the area of the steps 10, 11. Each clamping jaw 7 carries such a pin 12 each above and below the spacer member 8, i.e., the instrument 1 has, as a whole, four such pins 12, which extend in parallel to one another and are substantially shorter than the spacer members 8.

A sleeve 13 surrounding the bar 3 is mounted on the bar 3 rotatably around the longitudinal axis of the bar 3, and the sleeve 13 is screwed onto a threaded section of the bar 3 with its end 14 facing away from the handle 2, so that it is moved in the longitudinal direction of the bar 3 during the screwing on this threaded section. With its distal end facing away from the handle 2, the sleeve 13 surrounds the two arms 5, 6 in the section 15 directly adjoining the clamping jaws 7, and the arms 5, 6 are laterally widened in this section 15 such that they form obliquely extending stop faces 16 on both sides. When the sleeve 13 is fed on the threaded section in the direction of the clamping jaws 7, it slides along at these stop faces 16 and, as a result, pivots the arms 5, 6 against each other, i.e., the longitudinal slot 4 becomes narrower as a result.

Figure 2:
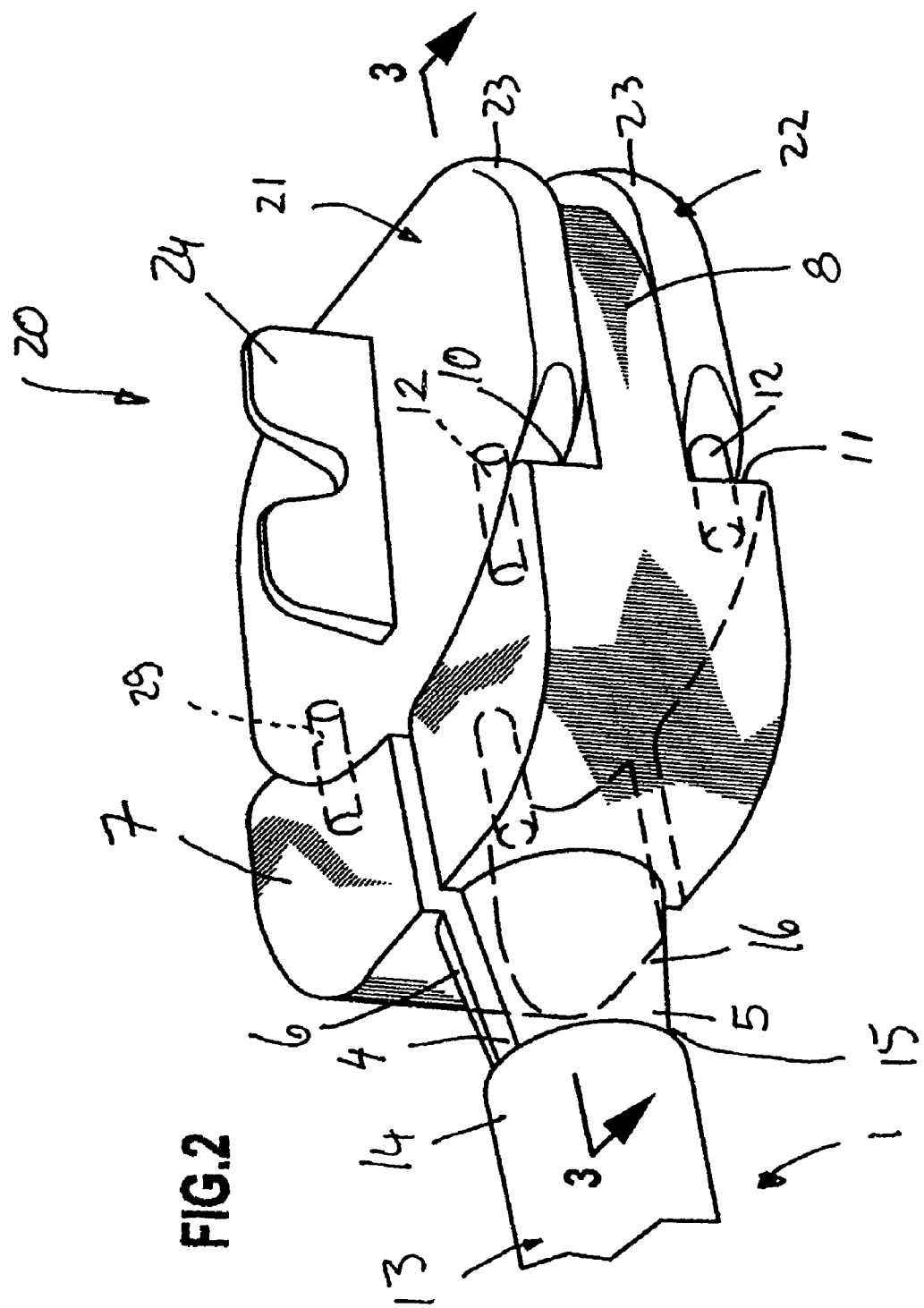
FIG. 2 shows an enlarged detail of the distal end of the surgical instrument according to FIG. 1 with a two-part intervertebral implant being held at it.
Figure 3:
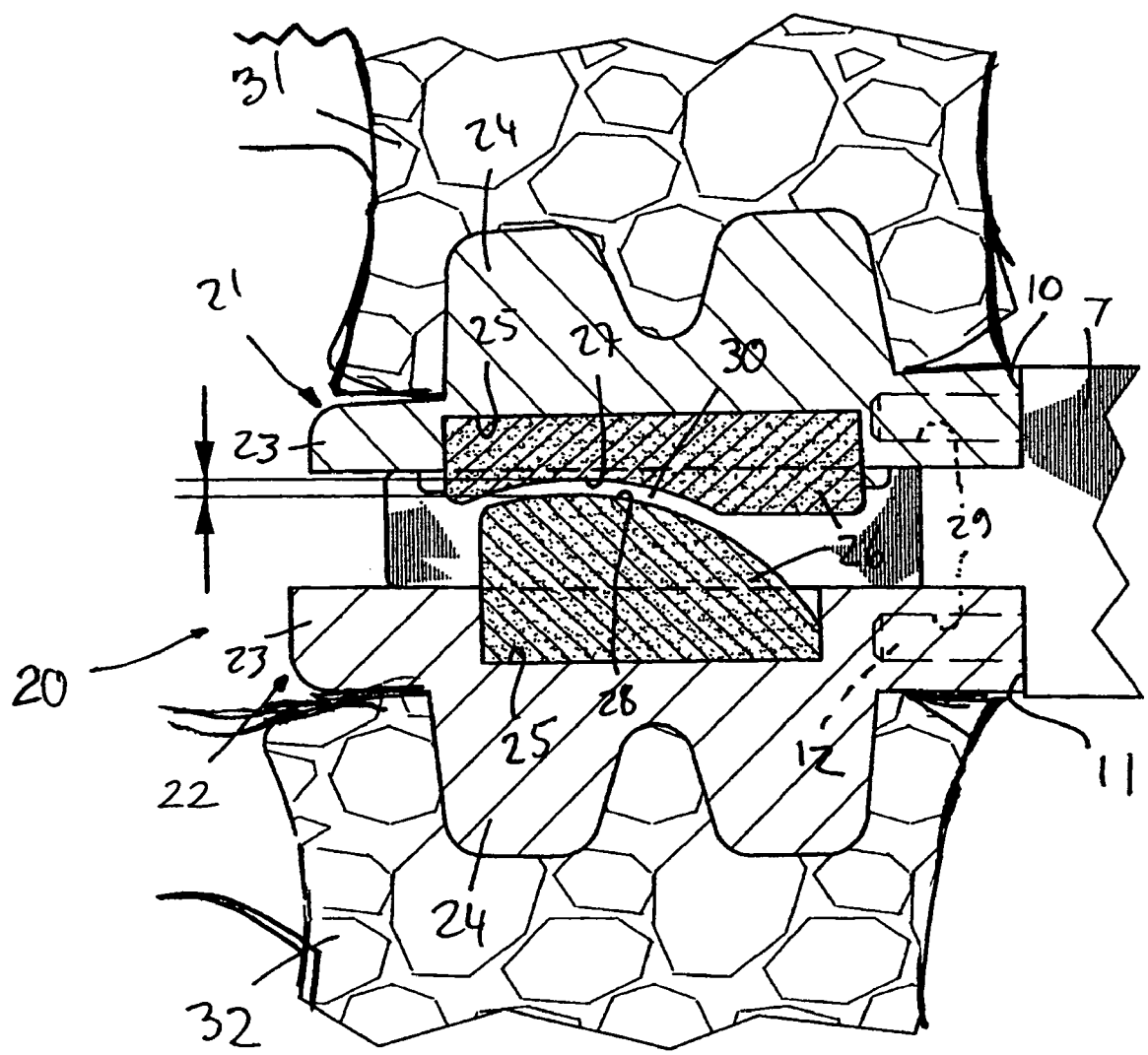
FIG. 3 shows a sectional view along line 3-3 in FIG. 2.

Referring to FIGS. 2 and 3, the instrument 1 is used to receive an implant 20, which comprises two parts 21, 22. Both parts have a flat, plate-shaped carrier 23, each of which carries an anchoring projection 24 on its outer side, while a ceramic inlay 26 is inserted into a depression 25 on the inner side. While the carriers 23 have essentially the same design, the ceramic inlays 26 have cooperating joint surfaces 27, 28, which are substantially partial spherical surfaces; one joint surface 27 is concave and the other joint surface 28 is convex; and both joint surfaces 27 and 28 are complementary to one another and, when they are flatly in contact with one another, they make possible the pivotable supporting of the two parts 21, 22 in relation to one another.

Both carriers 23 have two blind holes 29, which extend in parallel to one another and are used to receive the pins 12 of the instrument 1. The mutual distance between the blind holes 29 at one carrier 23 corresponds to the mutual distance between the pins 12 at opposite clamping jaws 7 when the arms 5, 6 are not pivoted, so that the pins 12 can be easily pushed into the corresponding blind holes 29 of the carriers 23 before the sleeve 13 is pushed forward. The carriers 23 are now held on the pins 12 and abut against the steps 10 of the clamping jaws 7, thereby limiting the depth of immersion of the pins 12.

The dimensions and the arrangements of the pins 12, of the blind holes 29, as well as of the spacer members 8 are selected to be such that after the carriers 23 have been pushed over the pins 12, the components are held at closely spaced locations from one another, so that the joint surfaces 27, 28 do not touch each other, have a short distance between them, and the gap 30 between the joint surfaces 27 and 28 is not wide, the width being, e.g., between 0.2 mm and 2 mm. This distance 30 between the joint surfaces 27 and 28 is facilitated and maintained because the spacer members 8 extend between the two carriers 23 and the carriers 23 with their inner surfaces facing each other lie on these spacer members 8, so that a further approach of the joint surfaces 27, 28 is prevented from occurring with certainty even under mechanical stress on the carriers 23. The spacer members 8 lie on opposite sides of the joint surfaces 27 and 28 and of the ceramic inlays 26, so that the ceramic inlays 26 are protectingly received between the two spacer members 8.

The carriers 23 can be fixed in this state, in which they are pushed over the arms 5, 6, by the sleeve 13 being pushed forward by screwing in the direction of the clamping jaws 7, and the sleeve 13 then comes into contact with the stop faces 16 and pivots the arms 5, 6 toward each other. As a result, the pins 12 in the blind holes 29 are tensioned against each other, clamping is brought about, and the carriers 23 are held securely at the clamping jaws 7.

When the implant 20 is fixed at the instrument 1 in this manner, the implant 20 can be handled safely and reliably by means of the instrument 1, and, in particular, the implant can be pushed in this manner into an intervertebral space between two vertebral bodies 31, 32, and the pushing in can be supported by blows with a hammer, which are exerted on the rear side of the handle 2. The instrument 1 of the present invention ensures that the forces of impact cannot cause damage to the joint surfaces 27, 28.

More specifically, it may be necessary during the insertion of the prosthesis 20 into the intervertebral space between vertebral bodies 31, 32 to strike the handle 2 of the inserting instrument 1 with a hammer in order to bring the prosthesis 20 into the desired position. Since ceramic is relatively brittle and sensitive to shocks compared with other materials, impact pulses must be prevented from being transmitted via the ceramic ball and socket joint of ceramic inlays 26. The wedge-shaped design of the spacer members 8 is arranged at the working end of the instrument 1 for this purpose. When the intervertebral disk prosthesis 20 is mounted on the inserting instrument 1, a small distance 30 is formed between the joint surfaces 27, 28 of the ceramic inlays 26, so that these ceramic inlays 26 are just spaced apart from one another so as not to touch each other and cannot transmit any pulses during the driving-in operation.

After insertion, the clamping of the carriers 23 at the clamping jaws 7 is released by screwing back the sleeve 13, and the instrument 1 is then pulled off from the implant 20. The wedge-shaped design of the spacer members 8 facilitates such an extraction; in addition, this wedge shape may optionally enable adaptation to the geometry of the carriers 23, whose inner surfaces do not need to be absolutely parallel to one another, but may optionally also form a small angle with one another. During the extraction of the spacer members 8 from the intermediate space between the carriers 23, the carriers 23 are brought closer to one another to the extent that the joint surfaces 27, 28 come into contact with one another and thus support the adjacent vertebral bodies 31, 32 in relation to one another in an articulated manner via the carriers 23.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A surgical system comprising:
   an implant having a first part and a second part detachably connected to said first part, the first part adapted to directly engage a first vertebra, and the second part adapted to directly engage a second vertebra adjacent the first vertebra, said first part including a convex joint surface mounted thereon, and said second part including a concave joint surface mounted thereon and facing the convex joint surface; and
   an instrument comprising:
   a holding element detachably connecting said instrument with each of the first and second parts of the implant, and
   a spacer element extending between the first and second parts of the implant and maintaining a distance between the convex and concave joint surfaces, thereby preventing the joint surfaces from contacting each other;
   said spacer element comprising two spacer members for receiving the joint surfaces of the implant between them, said holding element and the parts of the implant each comprising respective clamping elements configured to be pushed into one another for a detachable connection, and braced against each other at right angles to the direction in which they are pushed in for said detachable connection, said spacer element extending between said clamping elements.

2. The system of claim 1, wherein said distance between the joint surfaces is between 0.2 mm and 2 mm when said spacer element extends between the parts of the implant.

3. The system of claim 1, wherein said spacer element is plate-shaped.

4. The system of claim 1, wherein said spacer element comprises a flat top side and a flat underside for facing the parts of the implant.

5. The system of claim 4, wherein said top side and said underside of said spacer element are slightly sloped in relation to one another.

6. The system of claim 1, wherein said spacer members extend in parallel to one another.

7. The system of claim 1, wherein said clamping elements are projections and apertures engaging one another.

8. The system of claim 7, wherein said projections and apertures are pins and holes receiving said pins.

9. The system of claim 1, wherein said clamping elements are displaceable at right angles to the direction in which they are pushed.

10. The system of claim 9, wherein the instrument comprises:
    two pivotable arms; and
    a tensioning device for pivoting said arms in relation to one another,
    said arms carrying said clamping elements of the first and second parts of the implant at free ends.

11. The system of claim 10, wherein said arms are elastically pivotable in relation to one another.

12. The system of claim 11, wherein said tensioning device is a sleeve comprising a longitudinal axis, said sleeve extending over said arms and adapted for movement along said arms.

13. The system of claim 12, wherein said sleeve is rotatable around said longitudinal axis for movement along said arms and is mounted to the instrument via a screw thread.

14. The system of claim 10, wherein each of said arms carries each of said spacer members.

15. The system of claim 13, wherein each of said arms carries at a free end a clamping jaw in which said clamping elements are arranged and which forms a stop, with which the first and second parts of the implant are in contact when said instrument and the implant are connected with one another.

16. A surgical system comprising:
    an implant having a first end plate and a second end plate, the first end plate including a convex joint surface directly mounted thereon and the second end plate having a concave joint surface directly mounted thereon, the first and second end plates being movable toward one another in a first direction to move the joint surfaces into direct engagement with one another; and
    an instrument detachably coupled with the first and second end plates, said instrument comprising a spacer element extending between and engaging the first and second end plates to fix the first and second end plates in a spaced-apart condition, forming a clearance space between the convex joint surface and concave joint surface, so that the convex joint surface is held out of contact with the concave joint surface, said spacer element comprising two spacer members for receiving the joint surfaces of the implant between them, said instrument comprising a holding element and the parts of the implant each comprising respective clamping elements configured to be pushed into one another for a detachable connection, and braced against each other at right angles to the direction in which they are pushed in for said detachable connection, said spacer element extending between said clamping elements, thereby bracing said clamping elements against each other in a direction that extends at right angles to the displacement of the parts of the implant.

17. The surgical system of claim 16, wherein the instrument comprises a first jaw and a second jaw, each of said first and second jaws being movable toward one another in a second direction generally perpendicular to the first direction to clamp onto and hold the first and second end plates in the spaced-apart condition.

18. The surgical system of claim 17, wherein said spacer element comprises a flat top side and a flat underside for facing the parts of the implant.

19. The surgical system of claim 16, wherein said distance between the joint surfaces is between 0.2 mm and 2 mm when said spacer element extends between the parts of the implant.

20. The surgical system of claim 16, wherein said spacer element is plate-shaped.

* * * * *

UNITED STATES PATENT AND TRADEMARK OFFICE
CERTIFICATE OF CORRECTION

PATENT NO. : 7,549,995 B2  Page 1 of 1
APPLICATION NO. : 10/886245
DATED : June 23, 2009
INVENTOR(S) : Robert Schultz It is certified that error appears in the above-identified patent and that said Letters Patent is hereby corrected as shown below:

On the title page, item (30), should read as follows:

Foreign Application Priority Data:

September 4, 2003 (DE) 203 10 433

July 8, 2003 (DE) 103 30 699

Signed and Sealed this

Nineteenth Day of October, 2010

David J. Kappos
*Director of the United States Patent and Trademark Office*